United States Patent [19]

Furukawa et al.

[11] Patent Number: 5,185,418
[45] Date of Patent: Feb. 9, 1993

[54] HYDROLYZABLE SILYL GROUP-CONTAINING AZO COMPOUND, PROCESS FOR PRODUCING THE SAME AND SILYL GROUP-CONTAINING VINYL POLYMER PRODUCED BY USING THE SAME

[75] Inventors: Hisao Furukawa; Katsuhiko Isayama; Yasushi Kato, all of Hyogo, Japan

[73] Assignee: Kanegafuchi Kagaku Kogyo Kabushiki Kaisha, Osaka, Japan

[21] Appl. No.: 863,270

[22] Filed: Apr. 3, 1992

Related U.S. Application Data

[62] Division of Ser. No. 422,719, Oct. 17, 1989, Pat. No. 5,136,029.

[30] Foreign Application Priority Data

Oct. 20, 1988 [JP] Japan .................................. 63-265662

[51] Int. Cl.$^5$ .............................................. C08F 2/00
[52] U.S. Cl. .................................. 526/329.2; 526/194;
526/332; 526/328; 526/245; 526/318; 526/321;
526/287; 526/346; 526/293; 526/273; 526/264;
526/265; 526/303.1; 526/304; 526/306;
526/262; 526/320; 526/271; 526/249; 526/254;
526/255; 526/279
[58] Field of Search .................. 526/194, 329.2, 332,
526/328, 245, 318, 321, 287, 346, 293, 273, 264,
265, 303.1, 304, 306, 320, 271, 262, 249, 254,
255, 279

[56] References Cited

U.S. PATENT DOCUMENTS

| | | | |
|---|---|---|---|
| 3,775,386 | 11/1973 | Citron .................................. | 534/726 |
| 3,778,430 | 12/1973 | Citron .................................. | 534/726 |
| 4,118,367 | 10/1978 | Dawes et al. ..................... | 534/726 X |
| 4,316,041 | 2/1982 | Totten et al. ..................... | 534/577 X |
| 4,618,653 | 10/1986 | Kawakubo et al. ................ | 525/404 |

OTHER PUBLICATIONS

March, "Advanced Organic Chemistry", 3rd Ed., John Wiley and Sons, New York 1985 pp. 791–792, 802–803.

*Primary Examiner*—Joseph L. Schofer
*Assistant Examiner*—N. Sarofim
*Attorney, Agent, or Firm*—Armstrong, Westerman, Hattori, McLeland & Naughton

[57] ABSTRACT

A hydrolyzable silyl group-containing azo compound is represented by the following general formula (I):

$$A\left(Y-\overset{O}{\underset{\|}{C}}=\overset{H}{\underset{|}{N}}-R^2\overset{R^1_{3-m}}{\underset{|}{Si}}-X_m\right)_n \quad (I)$$

wherein A represents a group originating from an azo compound having one or more active hydrogen groups;
R$^1$ represents a monovalent organic group;
R$^2$ represents a divalent organic group;
X represents a hydrolyzable group;
Y represents —O—, —S—, $$-\overset{O}{\underset{\|}{C}}-O-, \text{ or } -\overset{H}{\underset{|}{N}}-;$$

m is an integer of 1 to 3; and
n is an integer of 1 or 2;

and process for producing the same is disclosed. The hydrolyzable silyl group-containing azo compound is used to prepare a hydrolyzable silyl group-containing vinyl polymer produced by polymerizing vinyl monomer as a radical polymerization initiator.

2 Claims, 1 Drawing Sheet

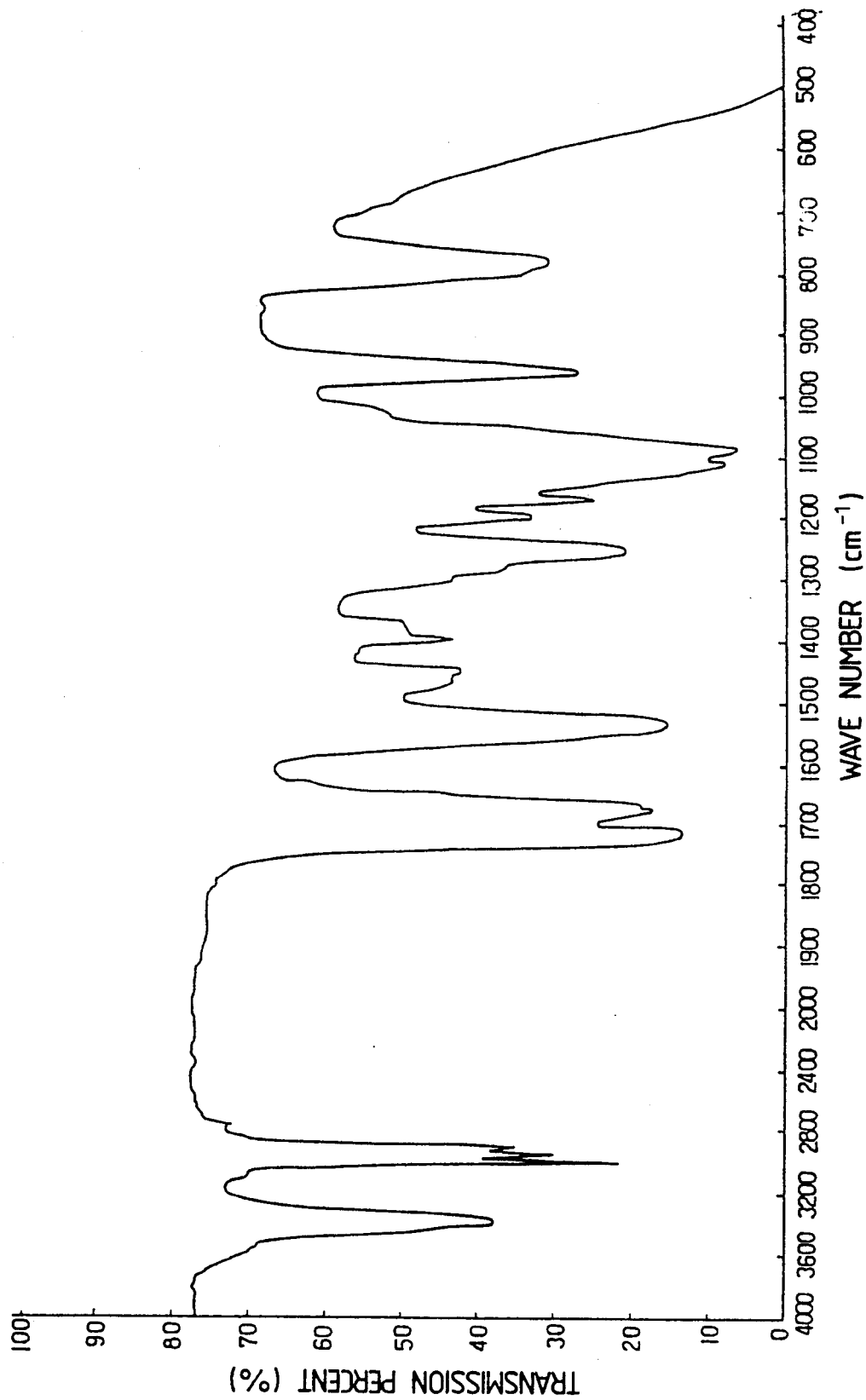

HYDROLYZABLE SILYL GROUP-CONTAINING AZO COMPOUND, PROCESS FOR PRODUCING THE SAME AND SILYL GROUP-CONTAINING VINYL POLYMER PRODUCED BY USING THE SAME

This is a division of application Ser. No. 07/422,719 filed Oct. 17, 1989 now U.S. Pat. No. 5,136,029.

FIELD OF THE INVENTION

This invention relates to a hydrolyzable silyl group-containing azo compound process for producing the same and a hydrolyzable silyl group-containing vinyl polymer produced by polymerizing vinyl monomer(s) with the use of said hydrolyzable silyl group-containing azo compound as a polymerization initiator.

BACKGROUND OF THE INVENTION

It is known that various functions can be imparted to a vinyl polymer by introducing various functional groups to the molecular terminals of said vinyl polymer and utilizing said functional groups by, for example, crosslinking said vinyl polymer or formulating the same into dispersed particles.

According to JP-B-43-16147 (the term "JP-B" as used herein means an "examined Japanese patent publication"), for example, an acrylic copolymer having an carboxyl group at a molecular terminal is synthesized by using 4,4'-azobis(cyanovaleric acid) and thioglycolic acid as a polymerization initiator and a chain transfer agent respectively in order to stabilize or crosslink said copolymer.

To obtain a hydrolyzable silyl group-containing vinyl copolymer, on the other hand, we have proposed to use a mercaptoalkylsilane as a chain transfer agent (JP-A-57-36109 (the term "JP-A" herein means an "unexamined published Japanese patent application"). However this method has disadvantages. For example, when the chain transfer agent is used alone, the amount of the hydrolyzable silyl groups which can be introduced into the molecular end of the vinyl polymer is limited. Further, the use of a large amount of the mercaptoalkylsilane would lower the weathering resistance of the resulting vinyl polymer.

We have conducted extensive studies in order to solve the above problems. As a result, we have completed the present invention.

SUMMARY OF THE INVENTION

The present invention relates to a hydrolyzable silyl group-containing azo compound represented by the following general formula (I):
wherein A represents a group originating from an azo compound having one or more active hydrogen groups;
$R^1$ represents a monovalent organic group;
$R^2$ represents a divalent organic group;
X represents a hydrolyzable group;
Y represents —O—, —S—,

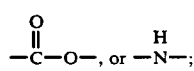

m is an integer of 1 to 3; and
n is an integer of 1 or 2.

The present invention also relates to a hydrolyzable silyl group-containing vinyl polymer which is produced by polymerizing vinyl monomer(s) with the hydrolyzable silyl group-containing azo compound as a radical polymerization initiator.

BRIEF DESCRIPTION OF THE DRAWING

FIG. 1 is a chart showing the infrared absorption spectrum of the azo compound obtained in Example 1 according to the present invention.

DETAILED DESCRIPTION OF THE INVENTION

The hydrolyzable silyl group-containing azo compound of the present invention is a compound represented by the following formula (I).

In formula (I), A is a group originating from an azo compound having one or more active hydrogen groups when the azo compound is reacted with an isocyanate group.

The azo compound having one or more active hydrogen groups, from which the group A originates, is not particularly restricted so long as it has one or more active hydrogen groups. Such groups include primary amino, secondary amino, hydroxyl, carboxyl, thiol and amide groups. It is preferable that the azo compound has 1 to 8 active hydrogen groups.

Particular examples of the azo compound include the following, though the present invention is not restricted to these examples:

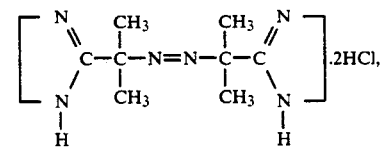

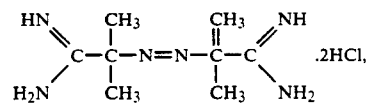

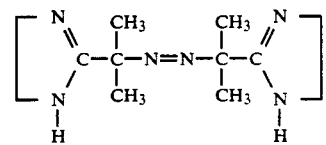

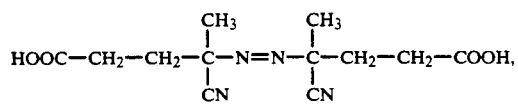

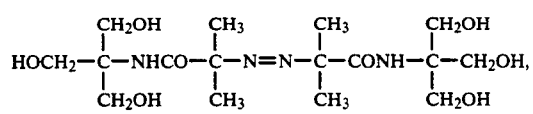

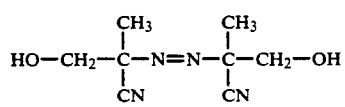

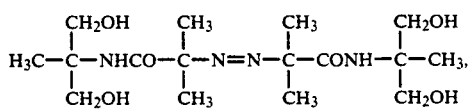

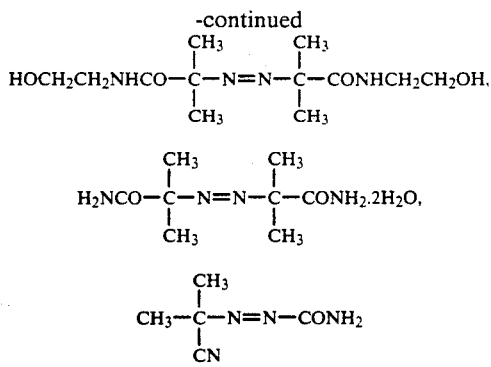

-continued

In formula (I) above, $R^1$ is a monovalent organic group such as alkyl groups having 1 to 10 carbon atoms, aryl and aralkyl groups. When two $R^1$ groups are present, they may be either the same or different.

Examples of alkyl groups having 1 to 10 carbon atoms include methyl, ethyl, butyl and cyclohexyl groups. An example of the aryl group is a phenyl group, and an example of the aralkyl group is a benzyl group.

In formula (I) above, $R^2$ is a divalent organic group such as alkylene groups having 1 to 10 carbon atoms, arylene groups or divalent aralkyl group.

Examples of the alkylene group having 1 to 10 carbon atoms include methylene, ethylene and propylene groups.

In formula (I) above, X is a hydrolyzable group such as a halogen atom or alkoxy, phenoxy, acyloxy, RS-group; wherein R is an alkyl group or an alkyleneoxy group. When 2 of 3 X groups are present, they may be either the same or different.

Examples of the above alkoxy group include methoxy and ethoxy groups.

In formula (I) above, "m" is an integer of 1 to 3.

In formula (I) above, "n" is an integer of 1 or greater but does not exceed the number of the active hydrogen groups contained in the azo compound having one or more active hydrogen groups from which group A originates. Generally, "n" is usually 1 or 2.

The compound represented by formula (I) above may be obtained, for example, by reacting the azo compound having one or more active hydrogen groups with a hydrolyzable silyl group-containing compound having an isocyanate group represented by formula (II):

wherein $R^1$, $R^2$, X, and m are as defined above.

Examples of compounds represented by formula (II) above include γ-isocyanatopropyl trimethoxysilane, γ-isocyanatopropyl triethoxysilane, γ-isocyanatopropylmethyl dimethoxysilane and γ-isocyanatopropylmethyl diethoxysilane, though it is not restricted thereby.

The azo compound having one or more active hydrogen groups is preferably reacted with the compound of formula (II) above at a temperature lower than the temperature of 10 hours half-life and as low as possible so as to minimize the radical decomposition of the azo compound.

In order to lower the reaction temperature, a catalyst which accelerates the reaction between the active hydrogen groups and the isocyanato group may be used.

Examples of such a catalyst include tertiary amines such as dimethyldodecylamine, triethylamine and triethylenediamine and organotin compounds such as dibutyltin dilaurate and tin octylate.

In the above-mentioned reaction, it is preferable that the molar ratio of the isocyanato group contained in the compound of formula (II) relative to the active hydrogen group contained in the azo compound ranges from 0.8:1 to 1.2:1.

The above reaction may be conducted either with or without a solvent. When a solvent is used, it is preferable that the solvent is free of active hydrogen groups. Examples of such a solvent include toluene, xylene, butyl acetate and methyl ethyl ketone. When an aromatic solvent such as toluene is used, the moisture present can be removed by azeotropic distillation prior to the reaction.

The silyl group of the resulting hydrolyzable silyl group-containing azo compound is bound to the azo compound by various bonds depending on the active hydrogen groups in the azo compound used. When an active hydrogen group is a primary or secondary amino group, for example, the bond created is a urea bond. When the active hydrogen group is a hydroxyl or a thiol group, the bond created is a urethane or a thiocarbamate bond respectively.

Thus the hydrolyzable silyl group-containing azo compound of the present invention can be synthesized.

The hydrolyzable silyl group containing azo compound of the present invention obtained is a novel compound. When it is used as a radical polymerization initiator optionally together with a chain transfer agent having hydrolyzable silyl group(s), which will be called a specific chain transfer agent hereinafter, a novel terecheric vinyl polymer having hydrolyzable silyl group at a molecular end can be obtained.

A telechelic structure is characterized in that a uniform crosslinked structure can be obtained from a crosslinked polymer having the same; and that a crosslinkable functional group located at a molecular end can efficiently contribute to crosslinking.

On the other hand, a hydrolyzable silyl group forms a crosslinked structure via a two-stage reaction comprising hydrolysis and condensation to thereby form a more stable siloxane bond. Thus the weathering and thermal resistance of the resulting crosslinked polymer can be improved.

The hydrolyzable silyl group-containing vinyl polymer of the present invention can be obtained by radical polymerizing or radical copolymerizing vinyl monomer(s) with the use of the hydrolyzable silyl group-containing azo compound of the present invention as a polymerization initiator optionally together with a specific chain transfer agent.

The polymerization may be either bulk, solution, nonaqueous dispersion or emulsion polymerization.

The vinyl monomers to be used in the production of the vinyl polymer of the present invention are not particularly restricted. Examples thereof include unsaturated carboxylates such as methyl (meth)acrylate [(meth)acrylate means an acrylate or a methacrylate, the same will apply hereinafter], ethyl (meth)acrylate, butyl (meth)acrylate, isobutyl (meth)acrylate, tertbutyl (meth)acrylate 2-ethylhexyl (meth)acrylate, lauryl (meth)acrylate, stearyl (meth)acrylate, benzyl (meth)acrylate, cyclohexyl (meth)acrylate, trifluoroethyl (meth)acrylate, pentafluoropropyl (meth)acrylate and diesters or half esters of unsaturated polycarboxylates such as maleic, fumaric and itaconic acids with straight or branched-chain alcohols having 1 to 20 carbon atoms; aromatic hydrocarbon vinyl compounds such as styrene, α-methylstyrene, chlorostyrene, styrene sulfonate, 4-hydroxystyrene and vinyltoluene; vinyl esters and allyl compounds such as vinyl acetate, vinyl propionate and diallyl phthalate; nitrile group-containing vinyl compounds such as (meth)acrylonitrile; epoxy group-containing vinyl groups such as glycidyl (meth)acrylate; vinyl compounds containing amino group(s) or the like such as dimethylaminoethyl (meth)acrylate, diethylaminoethyl (meth)acrylate, vinylpyridine and aminoethyl vinyl ether; vinyl compounds containing amido group(s) or the like such as (meth)acrylamide, diacetone (meth)acrylamide, itaconic diamide, α-ethyl (meth)acrylamide, crotonamide, maleic diamide, fumaric diamide, N-vinylpyrrolidone, N-butoxymethyl(meth)acrylamide, N,N-dimethylacrylamide, N-methylacrylamide and acrylomorpholine; hydroxyl group-containing vinyl compounds such as 2-hydroxyethyl (meth)acrylate, 2-hydroxypropyl (meth)acrylate, 2-hydroxyethyl vinyl ether, N-methylol (meth)acrylamide, Aronix 5700 (mfd. by Toagosei Chemical Industry, Co., Ltd.) and Placcel FA-1, FA-4, FM-1 and FM-4 (each mfd. by Daicel Chemical Industries, Ltd.); unsaturated carboxylic anhydrides such as (meth)acrylic acid, maleic acid, fumaric acid, itaconic acid, salts thereof (alkaline metal salts, ammonium salts, amine salts etc.) and maleic anhydride; vinyl compounds such as vinyl chloride, vinylidene chloride, chloroprene, propylene, butadiene, ethylene, isobutylene, isoprene, maleimide, N vinyl imidazole and vinyl sulfonate; fluoroolefins such as $CF_2=CF_2$, $CHF=CF_2$, $CH_2=CF_2$, $CH_2=CHF$, $CClF=CF_2$, $CHCl=CF_2$, $CCl_2=CF_2$, $CClF=CClF$, $CHF=CCl_2$, $CH_2=CClF$, $CCl_2=CClF$, $CF_3CF=CF_2$, $CF_3CF=CHF$, $CF_3CH=CF_2$, $CF_3CF=CH_2$, $CF_3CF=CHF$, $CHF_2CF=CHF$, $CF_3CH=CH_2$, $CH_3CF=CF_2$, $CH_3CH=CF_2$, $CH_3CF=CHF$, $CF_2ClCF=CF_2$, $CF_3CCl=CF_2$, $CF_3CF=CFCl$, $CF_2ClCCl=CF_2$, $CF_2ClCF=CFCl$, $CFCl_2CF=CF_2$, $CF_3CCl=CClF$, $CF_3CCl=CCl_2$, $CClF_2CF=CCl_2$, $CCl_3CF=CF_2$, $CF_2ClCCl=CCl_2$, $CFCFCl_2CCl=CCl_2$, $CF_3CF=CHCl$, $CClF_2CF=CHCl$, $CF_3CCl=CHCl$, $CHF_2CCl=CCl_2$, $CF_2ClCH=CCl_2$, $CF_3ClCCl=CHCl$, $CCl_3CF=CHCl$, $CF_2ICF=CF_2$, $CF_2BrCH=CF_2$, $CF_3CBr=CHBr$, $CF_2ClCBr=CH_2$, $CH_2BrCF=CCl_2$, $CF_3CBr=CHF$, $CF_3CH=CHBr$, $CF_2BrCH=CHF$, $CF_2BrCF=CF_2$, $CF_3CF_2CF=CF_2$, $CF_3CF=CFCF_3$, $CF_3CH=CFCF_3$, $CF_2=CFCF_2CHF_2$, $CF_3CF_2CF=CH_2CF_3CH=CHCF_3$, $CF_2=CFCF_2CH_3$, $CF_2=CFCF_2CH_3$, $CF_3CH_2CH=CH_2$, $CF_3CH=CHCH_3$, $CF_2=CHCH_2CH_3$, $CH_3CF_2CH=CHF$, $CFH_2CH=CHCFH_2$, $CH_3CF_2CH=CH_2$, $CH_2=CFCH_2CH_3$, $CF_3(CF_2)_2CF=CF_2$, $CF_3(CF_2)_3CF=CF_2$; vinyl ether compounds such as branched and straight chain alkyl vinyl ethers such as methyl vinyl ether, ethyl vinyl ether, propyl vinyl ether, isopropyl vinyl ether, butyl vinyl ether, tert-butyl vinyl ether, pentyl vinyl ether, hexyl vinyl ether, isohexyl vinyl ether, octyl vinyl ether and 4-methyl-1-pentyl vinyl ether, cycloalkyl vinyl ethers such as cyclopentyl vinyl ether and cyclohexyl vinyl ether, aryl vinyl ethers such as phenyl vinyl ether and o-, m- and p-tolyl vinyl ethers, benzyl vinyl ether and phenethyl vinyl ether; and hydrolyzable silyl group-containing vinyl compounds represented by the following formula (III):

wherein $R^3$ represents a monovalent hydrocarbon group selected from among an alkyl group having 1 to 10 carbon atoms, an aryl group and an aralkyl group; $R^4$ represents an organic group having a polymerizable double bond; and X and m are as defined above.

Any one of these vinyl monomers or a mixture of two or more of them may be used. In particular, the use of a hydrolyzable silyl group-containing vinyl compound makes it possible to introduce a hydrolyzable silyl group to a side chain of the vinyl polymer of the present invention.

Examples of the hydrolyzable silyl group-containing vinyl compounds represented by formula (III) above include

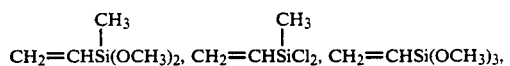

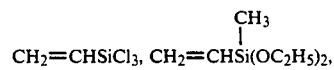

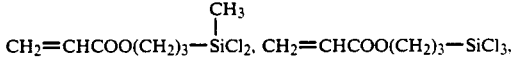

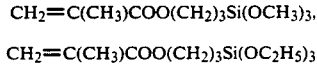

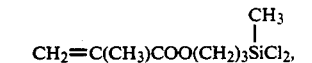

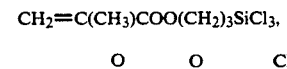

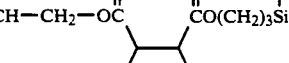

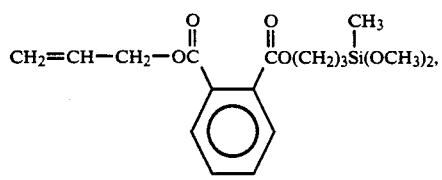

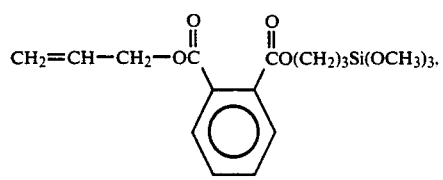

-continued

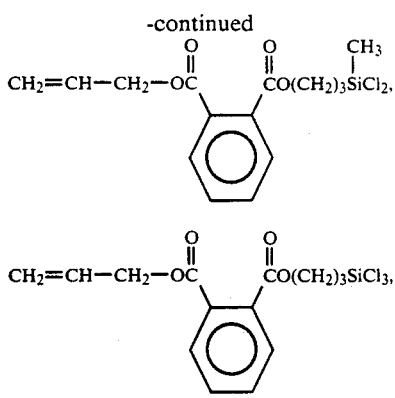

Examples of the hydrolyzable silyl group-containing chain transfer agent described above include γ-mercaptoporpyl trimethoxysilane, γ-mercaptoporpyl triethoxysilane, γ-mercaptopropylmethyl dimethoxysilane, γ-mercaptopropylmethyl diethoxysilane, γ-mercaptopropyl triisopropenyloxysilane, $(CH_3O)_3$—Si—S—S—Si$(OCH_3)_3$ and $(CH_3O)_3Si$—$(CH_2)_3$—S—S—$(CH_2)_3$—Si$(OCH_3)_3$ and tirchlorosilane.

In the production of the vinyl polymer of the present invention, the azo compound represented by formula (I) may be preferably used in an amount of 0.1 to 20 parts by weight per 100 parts by weight of the monomer mixture. Further, the specific chain transfer agent described above may be preferably used, if required, in an amount of 0.1 to 10 parts by weight per 100 parts by weight of the monomer mixture.

The polymerization temperature may be selected depending on the decomposition point of the azo compound of the present invention which is used as a polymerization initiator. It generally ranges from 0 to 200° C.

When solution polymerization is to be conducted, the solvent may be selected from among hydrocarbon solvents such as toluene, xylene, cyclohexane and n-octane; esters such as ethyl acetate and butyl acetate; ketones such as acetone, methyl ethyl ketone and methyl isobutyl ketone; amides such as dimethylformamide and dimethylacetamide; alcohols such as methanol, ethanol, isopropanol, n-butanol and ethylene glycol monoalkyl ethers; and mixtures thereof. It is particularly preferable to use an alcohol solvent, since the stability of the resulting polymer upon storage can be improved thereby.

The vinyl polymer of the present invention is a novel vinyl polymer in which hydrolyzable silyl groups are introduced by the above-mentioned novel radical polymerization initiator optionally together with a specific chain transfer agent.

It is known that polymerization of vinyl monomer(s) may be ceased by two methods, namely, disproportionation and recombination.

When a hydrolyzable silyl group is quantatively introduced into a molecular end of the vinyl polymer of the present invention, namely, telechelic reaction is to be conducted, a telechelic vinyl polymer comprising vinyl monomer(s) capable of recombination such as styrene, butadiene, acryonitrile or fluoroolefin/vinyl ether may be obtained by using the azo compound of the present invention as a radical polymerization initiator.

On the other hand, a vinyl polymer of a terecheric structure may be obtained by polymerizing a monomer where disproportionation is prior to recombination such as acrylic monomers with the use of the azo compound of the present invention together with a specific chain transfer agent to thereby elevate the ratio of the introduction of a silyl group to a molecular end of the polymer.

When the vinyl polymer of the present invention is to be used as a coating, or as a film or a molding material, its number average molecular weight preferably ranges from 1,000 to 10,000, still preferably from 1,000 to 50,000. When it is to be used as a sealant or a rubber material, its number-average molecular weight preferably ranges from 4,000 to 100,000, still preferably from 6,000 to 100,000.

It is known that a polymer having a crosslinkable functional group at a molecular end of one having such a functional group of a telechelic structure would form a uniform crosslinked structure when hardened. Thus these polymers, which would impart an excellent rubber elasticity to the resulting hardened product, are useful in combination with materials having a rubber elasticity such as rubber materials or sealants. Furthermore, it is known that a crosslinkable functional group located at a molecular end more efficiently contributes to crosslinking than functional groups located at a side chain.

The vinyl polymer of the present invention is available as, for example, rubber materials, sealants, films, coatings, adhesives, pressure-sensitive adhesives, potting materials or molding materials, since it would be crosslinked and hardened while forming a stable siloxane bond.

The vinyl polymer of the present invention may be hardened either with or without a hardening catalyst. A hardening catalyst, if used, may be selected from among alkyl titanates; acidic compounds such as phosphoric acid, p-toluenesulfonic acid and acidic phosphates; amines such as ethylenediamine and tetraethylenepentamine; organotin compounds such as dibutyltin dilaurate and dibutyltin maleate; basic compounds such as sodium hydroxide and sodium methylate; and others disclosed in JP-A-57-105446, and JP-A-59-124945.

The hardening catalyst may be used in amounts of 0.005 to 10 parts by weight, preferably 0.1 to 8 parts by weight, per 100 parts by weight of the polymer to be hardened.

Although the hardening proceeds at room temperature, it may be completed within a short period of time at an elevated temperature of 100° to 200° C.

The adhesiveness of the vinyl polymer of the present invention to various substrates may be improved by adding an aminosilane such as γ-aminopropyl trimethoxysilane or N-[β-aminoethyl]γ-aminopropyl trimethoxysilane; an epoxysilane such as γ-glycidoxypropyl trimethoxysilane; a product obtained by reacting aminosilane with an epoxy compound such as Epikote 828 or epoxysilane; or a partial hydrolyzate such as methyl orthosilicate, ethyl orthosilicate or methyl trimethoxysilane thereto.

A hydrolyzable ester may be used in the vinyl polymer of the present invention as a dehydrating agent. Examples of the hydrolyzable ester include methyl orthoformate, methyl orthoacetate, methyl orthosilicate, ethyl orthosilicate and methyl trimethoxysilane.

The vinyl polymer of the present invention is useful as, for example, rubber materials, sealants, coatings, adhesives, pressure-sensitive adhesives, films, potting materials and molding materials.

The hydrolyzable silyl group-containing azo compound of the present invention is a novel compound and is available as a radical polymerization initiator. By using this compound, the hydrolyzable silyl group-containing vinyl polymer of the present invention, which is preferably a telechelic polymer, can be readily produced. The polymer thus obtained has a high weathering resistance and is useful as, for example, rubber materials, sealants, coatings, adhesives, pressure-sensitive adhesives, films, potting materials and molding materials.

To further illustrate the present invention, the following Examples will be given. However it is to be understood that the present invention is not restricted to these examples and that any changes may be effected without departing from the spirit of the present invention. Unless otherwise indicated, all parts, percents and ratio are by weight.

EXAMPLE 1: SYNTHESIS OF HYDROLYZABLE SILYL GROUP-CONTAINING AZO COMPOUND

20 Grams of 2,2'-azobis[2-methyl-N-(2-hydroxyethyl)propionamide] in the form of pale yellow crystals was introduced into a reactor provided with a stirrer, a nitrogen inlet, a thermometer and a condenser. After adding 5 g of toluene thereto, the toluene was completely distilled off at 50° C. in vacuo to remove moisture. Next, 35 g of γ-isocyanatopropyl triethoxysilane and 0.1 g of dibutyltin dilaurate were added and the resulting mixture was allowed to react by stirring under a nitrogen atmosphere at 50° C. for 5 hours. As the reaction proceeded, the pale yellow crystals were dissolved. After the completion of the reaction, a pale yellowish green solution containing a trace amount of crystals was obtained.

The obtained solution was analyzed by infrared spectrometry. As a result, a peak of the isocyanato group at 2270 cm$^{-1}$ disappeared.

Toluene was added to the reactor and the unreacted azo compound was filtered off. Then the toluene was distilled off in vacuo to thereby give 53 g of a hydrolyzable silyl group-containing azo compound (A) in the form of a pale yellowish green solution.

The infrared absorption spectrum of the obtained azo compound (A) showed a peak of an urethane bond at 1530 cm$^{-1}$ that of —Si—O—C$_2$H$_5$ at 950 cm$^{-1}$ FIG. 1 shows the infrared absorption spectrum of the azo compound (A) determined on a rock salt plate.

Further the azo compound (A) was analyzed by GPC. As a result, it showed a single peak of 92% of an area ratio. Furthermore, the molecular weight of the azo compound (A) determined by VPO (vapor pressure osmometry) was 775.

These results indicate that the obtained hydrolyzable silyl group-containing azo compound (A) has the following structure.

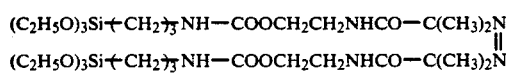

Molecular weight (calculated): 783.

EXAMPLE 2: SYNTHESIS OF HYDROLYZABLE SILYL GROUP-CONTAINING VINYL POLYMER 3.2 Grams of styrene, 10.3 g of n-butyl acrylate, 11.5 g of methyl methacrylate, 1.5 g of the azo compound (A) obtained in Example 1 and 11.4 g of xylene were introduced into a reactor provided with a stirrer, a nitrogen inlet and a thermometer. The mixture was polymerized by stirring under a nitrogen atmosphere at 110° C. for 4 hours to thereby give a colorless and transparent polymer solution.

The degree of polymerization was 99% while the number-average molecular weight of the obtained polymer was 18,000.

Then 100 parts, in terms of solid matter, of the obtained polymer was mixed with 2 parts of a hardening catalyst which was a mixture of 2-ethylhexyl acid phosphate and N,N-dimethyldodecylamine at a ratio by weight of 2:1. The mixture was formulated into a film of approximately 100 μm in thickness on a TEFLON plate with a spatula and then baked at 120° C. for 60 minutes.

The hardened film was colorless and transparent. The degree of gelation determined by acetone extraction was 75%. A film which bad been allowed to stand at room temperature for 24 hours without baking was also hardened.

EXAMPLE 3: SYNTHESIS OF HYDROLYZABLE SILYL GROUP-CONTAINING VINYL POLYMER 11.4 Grams of xylene, 10 g of ethyl vinyl ether and 2.0 g of the azo compound (A) obtained in Example 1 were introduced into a 100-cc stainless steel autoclave. The autoclave was degassed under reduced pressure by cooling to −78° C. with dry ice and methanol. Next, 15 g of chlorotrifluoroethylene was introduced into the autoclave followed by heating to 100° C. The mixture was reacted for 5 hours. After cooling, the unreacted monomer was removed to thereby give a colorless and transparent polymer solution.

The number-average molecular weight of the obtained polymer was 12,000.

100 parts by weight, in terms of dry matter, of the obtained polymer was mixed with 2 parts of hardening catalyst which was a mixture of 2-ethylhexyl acid phosphate and N,N dimethyldodecylamine at a ratio by weight of 2:1. The mixture was formulated into a film of a thickness of approximately 100 μm on a TEFLON plate with a spatula and baked at 120° C. for 60 minutes.

The hardened film thus obtained was colorless and transparent and had a high rubber-like strength. The degree of gelation determined by acetone extraction was 95%. A film which had been allowed to stand at room temperature for 24 hours without baking was also hardened.

While the invention has been described in detail and with reference to specific embodiments thereof, it will be apparent to one skilled in the art that various changes and modifications can be made therein without departing from the spirit and scope thereof.

What is claimed is:

1. A hydrolyzable silyl group-containing vinyl polymer which is produced by polymerizing vinyl monomer(s) using a hydrolyzable silyl group-containing azo compound as a radical polymerization initiator, said compound represented by formula (I):

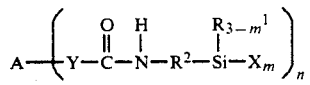

Wherein A represents a group originating from an azo compound having one or more active hydrogen groups selected from the group consisting of primary amino, secondary amino, hydroxyl, carboxyl, thiol and amide groups, and does not contain a phenyl group;

$R^1$ represents a monovalent organic group selected from the group consisting of alkyl groups having 1 to 10 carbon atoms, phenyl group and aralkyl group having 8 to 14 carbon atoms, and when two or more $R^1$ groups are present, they are the same or different;

$R^2$ represents a divalent organic group selected from the group consisting of an alkylene group having 1 to 10 carbon atoms, phenylene group and a divalent aralkyl group having 8 to 14 carbon atoms;

X represents a hydrolyzable group selected from the group consisting of a halogen atom, alkoxy having 1 to 3 carbon atoms, phenoxy group and acyloxy group having 1 to 4 carbon atoms wherein if two or more groups are present the groups are the same or different;

Y represents —O—, —S—,

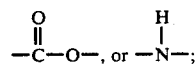

m is an integer of 1 to 3; and n is an integer of 2.

2. A hydrolyzable silyl group-containing vinyl polymer as claimed in claim 1, which is produced by further using a hydrolyzable silyl group-containing chain transfer agent during the polymerization of said vinyl monomer(s).